United States Patent [19]

Sirianne, Jr. et al.

[11] Patent Number: 5,598,837
[45] Date of Patent: Feb. 4, 1997

[54] PASSIVE HUMIDIFIER FOR POSITIVE AIRWAY PRESSURE DEVICES

[75] Inventors: Raymond A. Sirianne, Jr., Evergreen; Iain S. R. Smith, Boulder, both of Colo.

[73] Assignee: Respironics, Inc., Murrysville, Pa.

[21] Appl. No.: 467,017

[22] Filed: Jun. 6, 1995

[51] Int. Cl.$^6$ .................................................. A61M 16/16
[52] U.S. Cl. .............................. 128/204.14; 128/203.12; 261/119.1
[58] Field of Search .................. 128/203.12, 204.13, 128/204.14, 200.11, 200.24; 261/119.1, DIG. 4, DIG. 15, DIG. 34, DIG. 65; 237/78 R; 236/44 R; 55/244, 249

[56] References Cited

U.S. PATENT DOCUMENTS

| | | | |
|---|---|---|---|
| 4,655,213 | 4/1987 | Rapoport et al. | 128/205.25 |
| 4,807,616 | 2/1989 | Adahan | 128/204.21 |
| 5,117,819 | 6/1992 | Servidio et al. | 128/204.18 |
| 5,148,802 | 9/1992 | Sanders et al. | 128/204.18 |
| 5,231,979 | 8/1993 | Rose et al. | 128/204.14 |

OTHER PUBLICATIONS

Healthdyne Technologies' product brochure for "Tranquility Plus," undated.
Respironics, Inc. product brochure for "Humidifier" 1991.

Primary Examiner—V. Millin
Assistant Examiner—Eric P. Raciti
Attorney, Agent, or Firm—Reed Smith Shaw & McClay

[57] ABSTRACT

A passive humidifier for use with positive airway pressure devices including a chamber having an inlet and an outlet for holding a supply of water. Pressurized air is forced over a series of baffles arrayed within parallel channels inside the chamber for creating localized turbulence at the free water surface to maximize humidification efficiency. An accumulation chamber in communication with the outlet reduces the likelihood of water droplets escaping from the outlet.

3 Claims, 6 Drawing Sheets

PASSIVE HUMIDIFIER FOR POSITIVE AIRWAY PRESSURE DEVICES

FIELD OF THE INVENTION

The present invention relates to providing humidification to air supplied by continuous positive airway pressure devices and bi-level pressure devices used to treat sleep apnea.

BACKGROUND OF THE INVENTION

The sleep apnea syndrome afflicts an estimated 1% to 5% of the general population and is due to episodic upper airway obstruction during sleep. Those afflicted with sleep apnea experience sleep fragmentation and intermittent, complete or nearly complete cessation of ventilation during sleep with potentially severe degrees of oxyhemoglobin desaturation. These features may be translated clinically into extreme daytime sleepiness, cardiac arrhythmias, pulmonary-artery hypertension, congestive heart failure and/or cognitive dysfunction. Other sequelae of sleep apnea include right ventricular dysfunction with cor pulmonale, carbon dioxide retention during wakefulness as well as during sleep, and continuous reduced arterial oxygen tension. Hypersomnolent sleep apnea patients may be at risk for excessive mortality from these factors as well as by an elevated risk for accidents while driving and/or operating potentially dangerous equipment.

Continuous positive airway pressure (CPAP) devices have been developed to treat this disorder. CPAP devices deliver positive air pressure to the nasal passages of patients during sleep in order to maintain their airways in a continuously open state. Examples of sleep apnea treatments based on continuous positive airway pressure applied within the airway of the patient are disclosed in U.S. Pat. Nos. 4,655,213 and 5,117,819. Bi-level positive airway therapy for treatment of sleep apnea and related disorders is taught in U.S. Pat. No. 5,148,802. In bi-level therapy, pressure is applied alternately at relatively higher and lower prescription pressure levels. An improved apparatus for delivering pressurized air to the airway of a patient which includes a feedback/diagnostic system is described in U.S. patent application Ser. No. 08/378,467, the disclosure of which is hereby incorporated by reference. The above apparatus includes a feedback system having a sensor means which detects the patient's breathing patterns. Unlike other systems, the breathing pattern sensor is situated generally at the end of the breathing circuit remote from the patient.

A problem associated with positive airway pressure devices is a lack of moisture in the air delivered by these devices has a drying effect on patient airways which causes the patient to have considerable discomfort and difficulty sleeping.

Humidifiers have been developed for use with CPAP devices to humidify the air supplied to the patient. Currently-available passive humidifiers designed for this purpose typically have been little more than reservoirs partially filled with water through which the air circulates. The air passes over the water's meniscu and entrains whatever water vapor is available at or near the free water surface. The rate of evaporation is governed primarily by the internal energy of the water in the reservoir and the concentration gradient of water vapor in the direction normal to the free surface.

Because of the laminar nature in these prior devices the concentration gradient of water vapor normal to the free surface is relatively low. The average temperature of the water decreases with time because of the transfer of heat in the phase change at the surface. Hence, the internal energy of the water mass decreases with time, causing a decay in the rate of vaporization and, therefore, the humidity of the air delivered to the patient.

One humidifier of interest is disclosed in U.S. Pat. No. 4,807,616 comprises a humidifier body 100 including a heater 120 in the form of an electric 1 coil at the end of an insulating sleeve 122. The electrical coil is disposed so as to be totally immersed in the water within the body 100.

Another humidifier of interest is made by Respironics, Inc. of Murrysville, Pa., comprises a shallow water reservoir having an inlet and an outlet. Healthdyne Technologies produces a similar passover humidifier for use with CPAP systems which adds moisture to intake air as it flows over the water in the humidifier's channel maze.

A variation of the Respironics, Inc. humidifier is shown in U.S. Pat. No. 5,231,979 to Rose et al. The Rose patent discloses a humidifier having shelve and ledges disposed near the inlet and outlet for breaking up waves. A single baffle is used to create a U-shape. air pathway through the humidifier. In an embodiment which is not illustrated, a pair of spaced apart baffles may be used to create an essentially S-shaped or serpentine airflow path. Nevertheless, because the airflow enters, circulates through and exits the humidifier body substantially parallel to the water surface, the laminar and essentially unrestricted nature of the airflow suggests that such airflow could not create the air turbulence necessary to assure a robust rate of vaporization. The disclosed effect of the baffle is to produce a circulation in the air flow around the baffle, the "waves" of which flow are broken by shelves and ledges.

An advantage, therefore, exists for a humidifier in which waves are dissipated in advance of the outlet by baffles such that the shelves and ledges of Rose et al. are not needed. The simplistic design of Rose et al. requires these shelves and ledges to be directly beneath the outlet. In the present invention baffles and an accumulation chamber eliminate the need for such structure.

Another advantage exists, therefore, for a positive airway pressure device humidifier designed to increase localized air turbulence to yield a high vapor concentration gradient.

A further advantage exists for a total surface area of water in the humidifier which is significantly greater than that of current devices, further enhancing the rate of mass transfer.

SUMMARY OF THE INVENTION

The present invention provides a humidifier including a reservoir body having a plurality of parallel air flow channels each of which contain a series of baffles or spoilers extending essentially perpendicularly to the channels. The humidifier is passive in that no energy is added to or by the humidifier other than heat transfer from or to ambient air through the enclosure wall. Therefore, water temperature would change to obtain thermal equilibrium with the ambient air temperature. This change of water temperature changes, potentially decreasing, the initial energy of the water thus reducing humidification efficiency in passive devices. The concentration gradient then becomes increasingly important as a driving force for vaporization. Since the system is not truly adiabatic, however, some heat is transferred through the walls of the reservoir from surrounding air, thus, helping to reduce the vaporization heat loss. Maintaining the Reynolds number as high as possible helps improve humidification efficiency by increasing the vapor concentration gradient.

The present humidifier forces the flow of air to maintain a Reynolds number sufficient to yield a higher vapor concentration gradient. This is accomplished by forcing the air over a series of spoilers or baffles arrayed within parallel channels inside the device. The air undergoes several directional changes as it progresses through the channels: a combination of horizontal recirculation and vertical sinusoidal flow in the individual channels created by the lateral baffles and the longitudinal channel members. The horizontal recirculation increases the residence time of control volume of air over a given segment of the water's surface to allow dry air adequate time to absorb water vapor, while sinusoidal vertical motion helps maintain turbulence.

The present invention differs most noticeably from the prior art in its internal configuration. The prior art has a smooth interior while the present invention has a series of baffles arrayed perpendicularly to the direction of flow. The parallel channels aid in minimizing flow resistance while optimizing localized turbulence. The local velocity of the air is momentarily increased to cause a temporary elevation in the average Reynolds number as it passes over the spoilers while keeping the flow resistance at or below an acceptable level.

Another major advantage over the prior art is the presence of a chamber at the location of the humidifier's outlet port. This chamber serves as an accumulator for water and, in one embodiment, a means of minimizing air velocity over the water contained in it. The likelihood of introducing a bolus of water to the patient breathing circuit in the event that the device is tipped in the direction of the outlet port is thus reduced. The accumulation chamber is also capable of functioning as an acoustic chamber for instances when the humidifier is used in combination with a positive airway pressure device like that disclosed in copending U.S. patent application Ser. No. 08/378,467. In this type of system, any accessory such as humidifier may attenuate or absorb sound. In these instances, the accumulator chamber acoustically tunes the blower outlet sensor to heighten sensitivity to wave lengths of sound associated with snoring patterns and reduces background equipment and related noise by causing acoustic energy to resonate in the frequency range of interest rather than attenuating the sound as in a typical humidifier.

The primary benefit of the present invention is improved humidification efficiency without the use of an external energy source. This improvement is beneficial to the patient in that it provides an increase in comfort in a low ambient humidity environment, enabling the patient to fall asleep more easily. It also aids in diminishing the drying effects on patient airways which are a common problem in dry environments.

Another benefit is the added safety features intended to minimize the introduction of liquid water into the patient airway circuit.

Further benefits are accomplished by the present invention's unique two piece design formed by injection molding providing ease of cleaning, ease of assembly, a long useful life, manufacturability, ease of maintenance and low cost.

BRIEF DESCRIPTION OF THE DRAWINGS

The invention will become more readily apparent from the following description of preferred embodiments thereof shown, by way of example only, in the accompanying drawings, wherein.

DETAILED DESCRIPTION OF THE INVENTION

Figure 1:
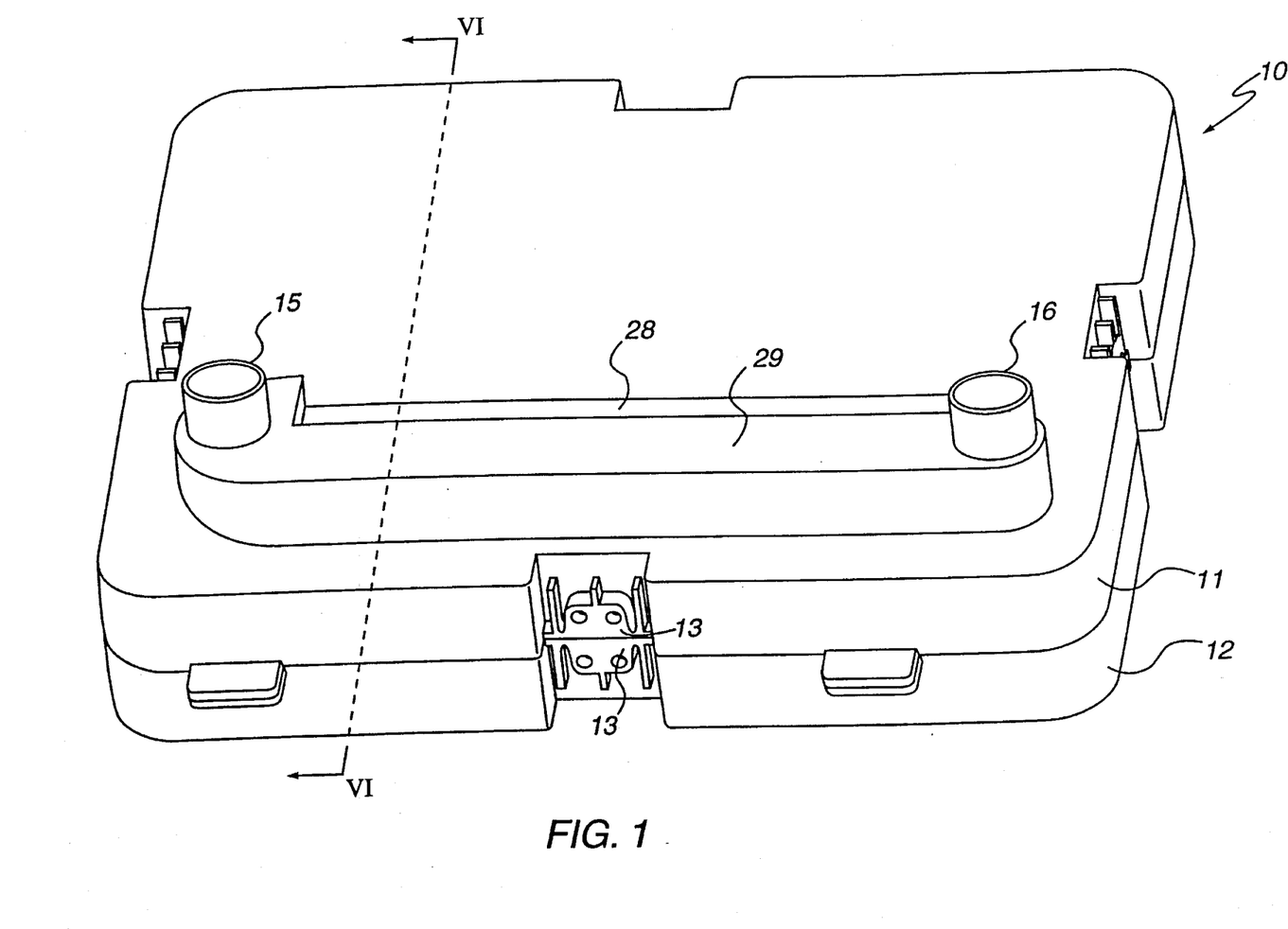
FIG. 1 is a perspective view of a humidifier of a first embodiment of the present invention showing a humidifier top and a humidifier base in assembled condition.

Turning to the drawings, a humidifier 10 in accordance with a presently preferred embodiment of the present invention is shown in FIG. 1. The humidifier 10 includes a top 11 and a base 12 which are connectable together by attachment means 13 in order to form a humidifier body for holding a supply of water. The top 11 includes a tubular inlet 15 and a tubular outlet 16. The inlet 15 is connectable to an air outlet of a positive airway pressure device (not illustrated). Positive air pressure is supplied by the device to the humidifier body by way of the humidifier inlet 15. The pressurize air from the positive airway pressure device circulates through the humidifier body, becomes humidified and exits the humidifier body through outlet 16. The now moisturized pressurized air is subsequently delivered to the patient through a hose (not illustrated) and a mask (also not illustrated). A positive pressure airway device useful with the humidifier 10 of the present invention is disclosed in copending application Ser. No. 08/378,467.

Figure 2:
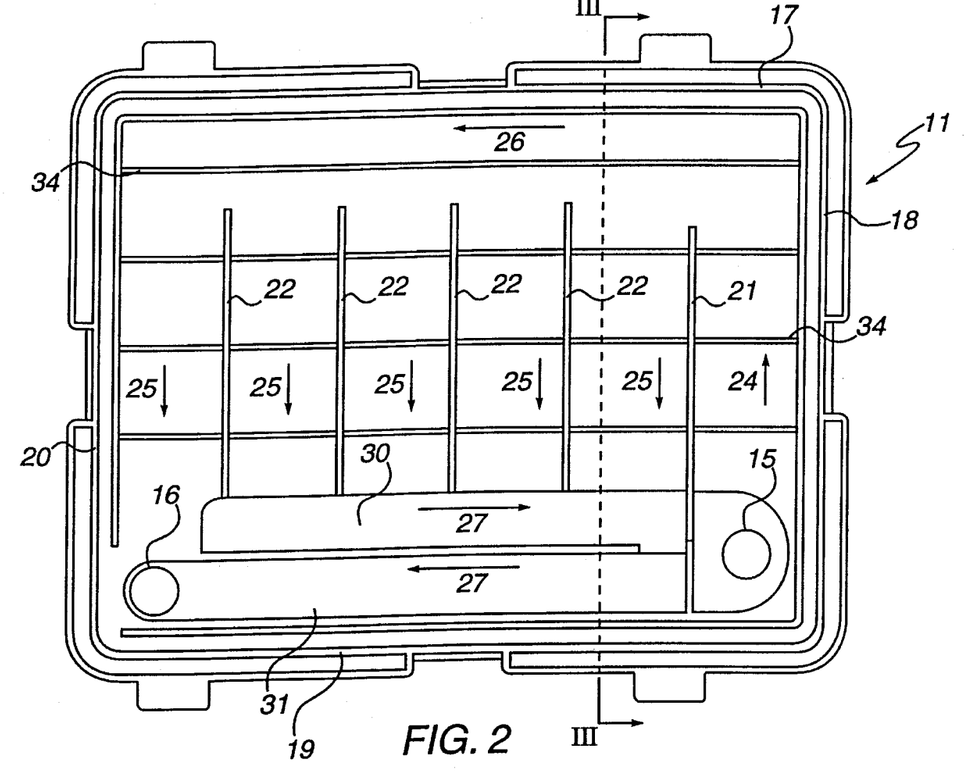
FIG. 2 is a plan view of the humidifier top of the first embodiment viewed from the bottom.
Figure 3:
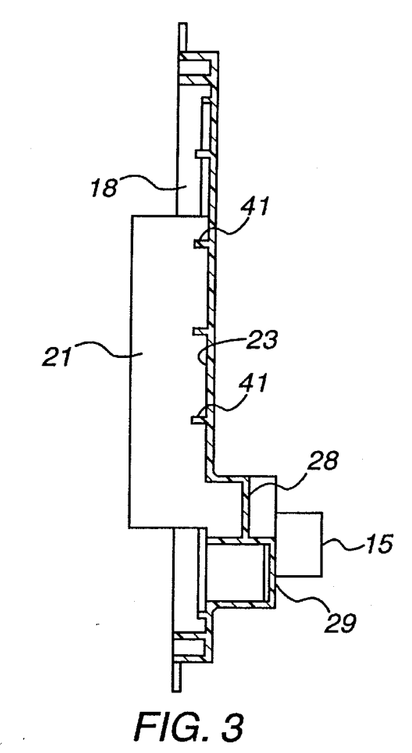
FIG. 3 is a cross-sectional end view of FIG. 2 as seen from line III—III of that figure.

The humidifier top 11, as shown in FIGS. 2 and 3, includes sidewalls 17, 18, 19, 20 and a plurality of channel walls 21, 22 extending substantially downwardly from a top wall 23. Channel walls 21, 22 extend substantially parallel to each other to form a plurality of air flow channels 24, 25. The air flow channels include a single inlet channel 24 and a plurality of outlet channels 25. Inlet channel 24 directs air which has entered the humidifier body away from the inlet 15. Outlet channels 25 direct air in the direction of the outlet 16. Channel walls 21, 22 extend substantially towards but do not come into contact with Opposite sidewalls 17, 19 of top 11. The inlet channel 24 is formed between channel wall 21 and sidewall 20. The outlet channels 25 are formed between the channel walls 21, 22 and sidewall 20. Air is directed from the inlet channel 24 into the outlet channels 25 by a first transverse air pathway 26 which is formed between sidewall 17 (including sidewall 34 of the base 12) and the ends of the channel walls 21, 22 nearest sidewall 17. A second transverse air pathway 27 is formed at the opposite ends of the channel walls 22. The second air pathway 27 is disposed within a chamber and directs air exiting from the outlet channels 25 towards the outlet 16. The second air pathway 27 is further defined by first and second raised chamber portions 28, 29 of top 11 forming a U-shafted air pathway 27. Air is directed from the outlet channels 25 and into a first leg 30 before entering a second leg 31 of the U-shaped pathway. Second leg 31 directs the air in the direction of outlet 16. The first leg 30 of the U-shaped pathway has an upper surface formed by the first raised chamber portion 28. The second leg 31 of the U-shaped pathway has an upper surface formed by the second raised chamber portion 29 which is raised at a level higher than first raised chamber portion 28. First leg 30 has a lower surface formed by the bottom wall 32 of base 12. Second leg 31 has a lower surface formed by a chamber floor member 33 which is situated at a level higher than the bottom wall 32.

The U-shaped pathway 27 serves as an accumulator chamber for water and a means of minimizing the discharge of water droplets through the outlet 16, thus, inhibiting the discharge of water droplets through the outlet 16. Also, the second leg 31 of the humidifier is capable of functioning as an acoustic chamber for instances when the humidifier 10 is in use with a positive airway pressure device of the type disclosed in copending application Ser. No. 08/378,467 in which the breathing pattern sensor is located at the end of the breathing circuit remote from the patient.

Other arrangements for the second air pathway 27 are also within the scope of the invention. It is also contemplated that the first leg 30 of the pathway could be eliminated for use with conventional CPAP or BiPAP systems.

Figure 4:
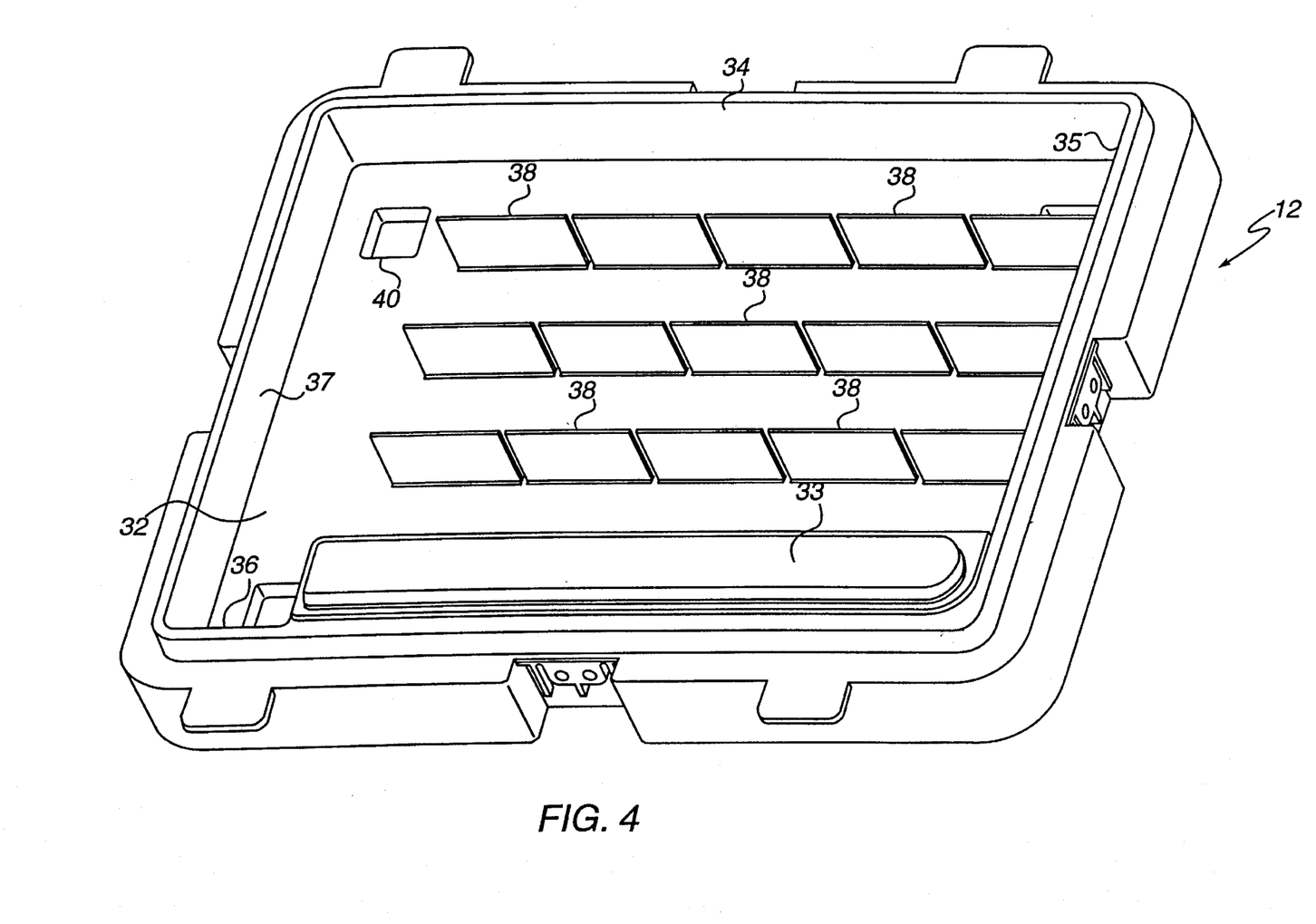
FIG. 4 is a perspective view of the humidifier base of the first embodiment.
Figure 5:
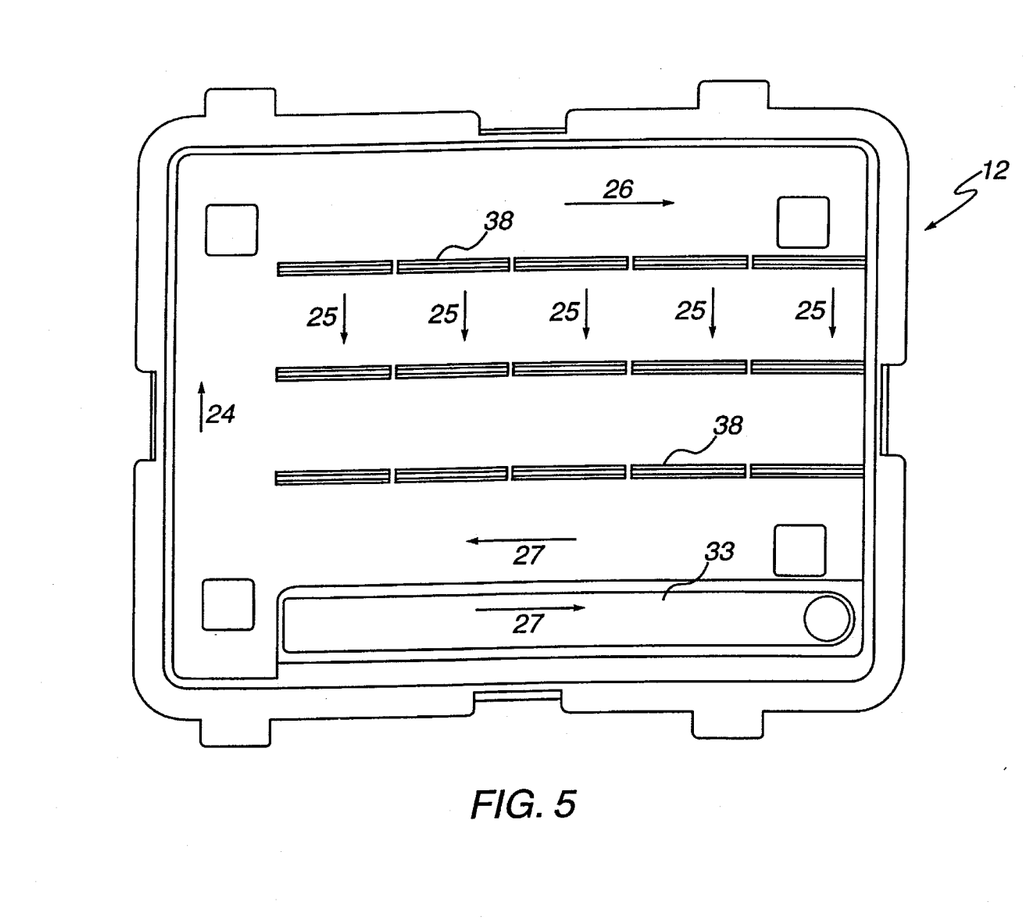
FIG. 5 is a plan view of the humidifier base of the first embodiment viewed from the top.
Figure 6:
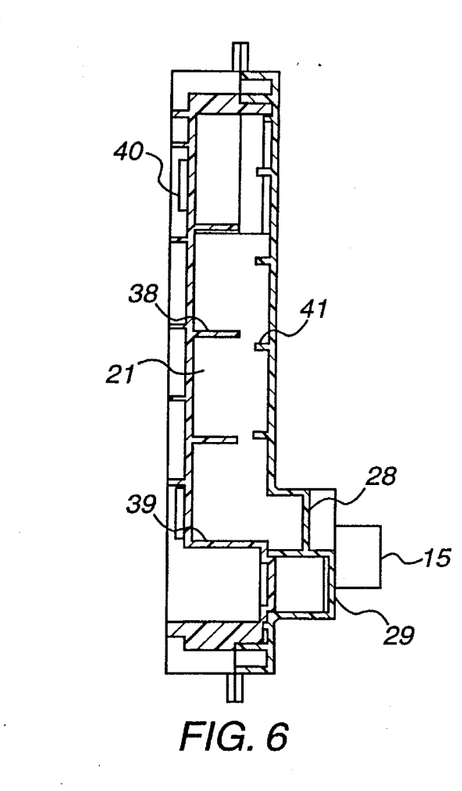
FIG. 6 is a cross-sectional end view of FIG. 1 as seen from VI—VI of that figure.

The humidifier base 12 is best seen in FIGS. 4 and 5. The humidifier base 12 includes sidewalls 34, 35, 36, 37 and a contiguous bottom wall 32 for holding a supply of water. Rows of spaced apart baffles 38 extend towards opposite sidewalls and substantially upwardly from the bottom wall 32. The rows of baffles 38 extend in a direction substantially transverse to the direction of the channels 24, 25 when assembled. Each transverse row of baffles has baffles 38 which correspond in number and location to the outlet channels 25. Thus, a baffle 38 from each transverse row is disposed in each of the outlet channels. The inlet channel 24 is free from baffles. The baffles 38 generally extend such that their upper ends are at a level higher than the free surface level of the supply of water. Thus, the air is forced over a series of baffles 38 within the parallel outlet channels 25. The air undergoes several directional changes through the channels: a combination of horizontal recirculation and vertical sinusoidal flow in the individual channels created by the lateral baffles 38 and the longitudinal channel walls 21, 22. This greatly increase, the vaporization of water by allowing adequate time for absorption and maintaining turbulence.

The base 12 further includes the chamber floor member 33 which forms the lower surface of second leg 31. The chamber floor member 33 is disposed at a height higher than the bottom wall 32 and the baffles 38. Chamber floor member 33 has an inner wall 39 which forms a side surface of first leg 30.

Base 12 further includes projections 40 to which rubber pads (not illustrated) may be attached for support.

The top 11 and base 12 are preferably formed by injection molding. But those skilled in the art will appreciate that other manufacturing methods are possible. The top 11 preferably has several rows of spaced apart ribs 41 which extend transversely to channels 24, 25. These ribs 41 serve to strengthen the planar surface of the top 11.

Figure 7:
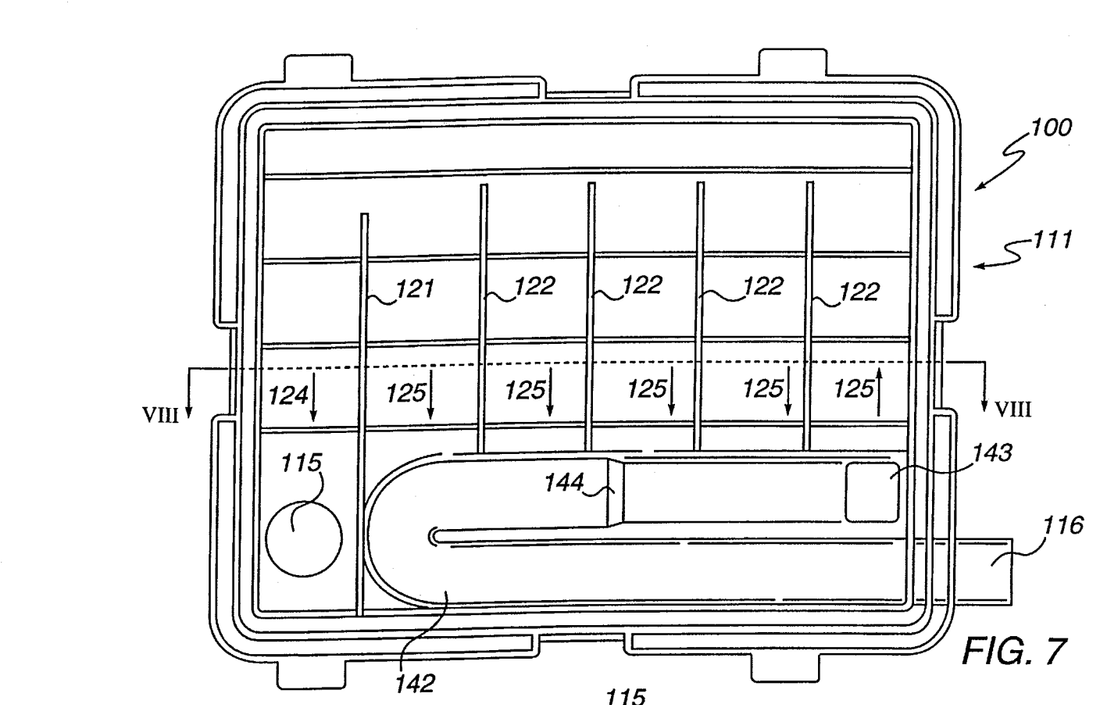
FIG. 7 is a plan view of a humidifier top of a second preferred embodiment viewed from the bottom.
Figure 8:
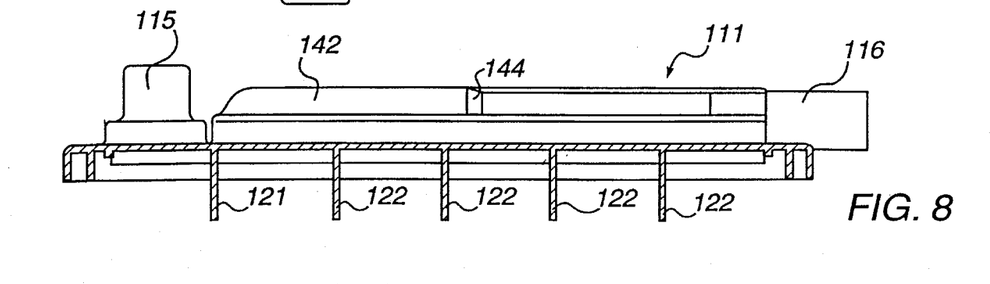
FIG. 8 is a cross-sectional view of FIG. 7 as seen from VIII—VIII of that figure.
Figure 9:
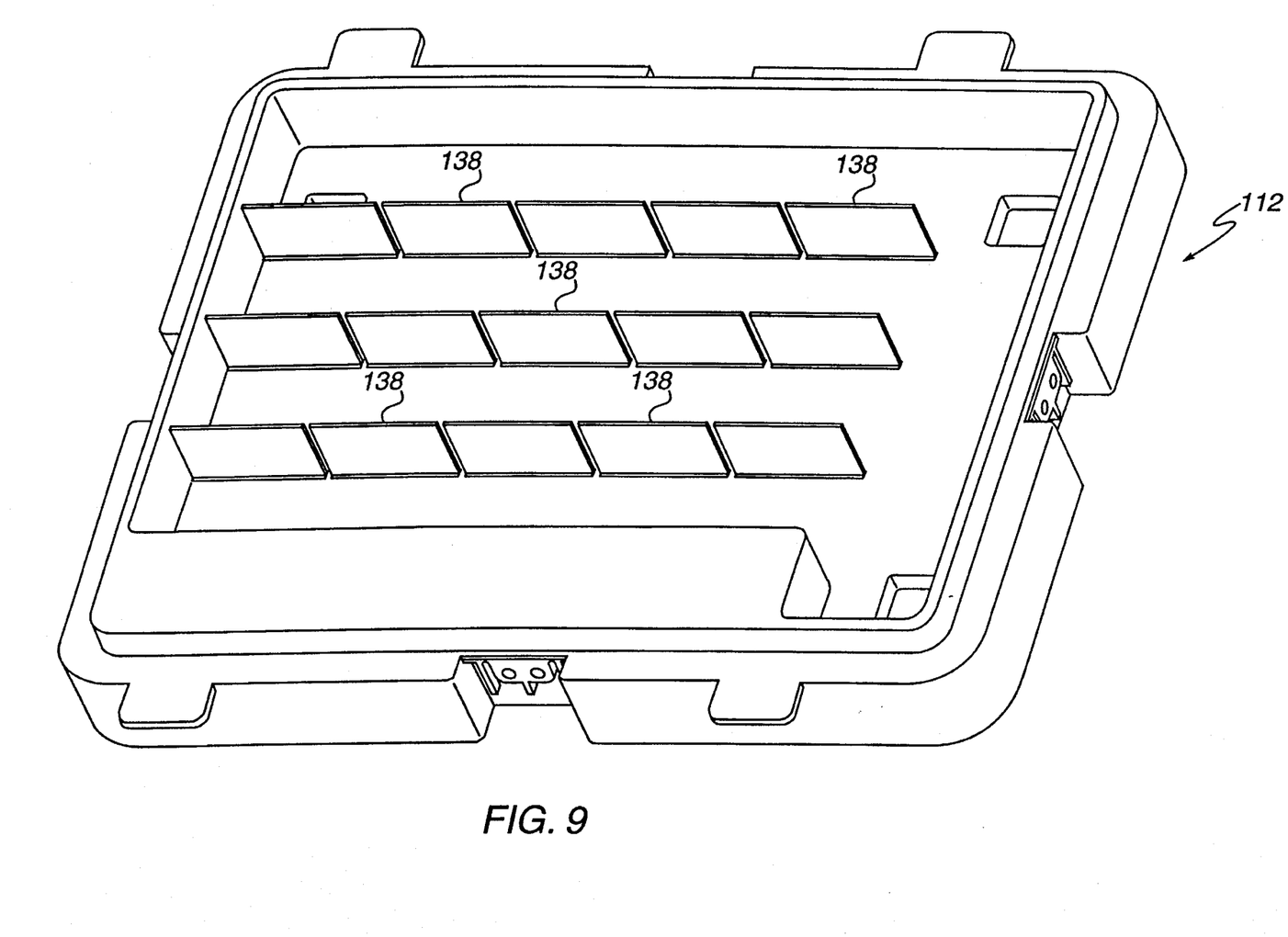
FIG. 9 is a perspective view of the humidifier base of the second embodiment.

A humidifier 100 in accordance with a presently preferred second embodiment of the present invention is shown in FIGS. 7–9. Pressurized air enters the humidifier 100 through inlet 115 circulates through the system of lateral baffles 138 in base 112 and longitudinal channels 124, 125 formed by channel walls 121, 122 and becomes humidified as in the first embodiment. In this embodiment, top 111 includes a U-shaped chamber 142 having a chamber inlet 143 and a laterally extending outlet 116.

While in the first embodiment the first leg 30 of the U-shaped pathway was open to the interior of the humidifier, the sole communication of the U-shaped chamber 142 of the second embodiment with the interior of the humidifier is through chamber inlet 143. Also, the first leg of the U-shaped chamber 142 has a diameter transition portion 144 wherein the diameter increases from a smaller diameter to a larger diameter. Both the chamber inlet 143 and the diameter transition portion function to help acoustically tune the snoring sound received from a patient in order to set the resonance frequency of the sound for instances when the humidifier is used in combination with a feedback/diagnostic system of the type disclosed in U.S. patent application Ser. No. 08/378,467. In this type of CPAP apparatus, the breathing pattern sensor is situated generally at an end of the breathing circuit remote from the patient. Thus, any type of accessory such as a humidifier may attenuate or absorb snore sound. The U-shaped chamber 142 is configured such that it causes acoustic energy to resonate in the frequency range which is known to be associated with upper airway obstructions rather than attenuating the sound as in a typical humidifier.

Although the present humidifier has been described for use with positive airway pressure devices, the invention can be used in conjunction with other types of breathing devices where humidification would be desirable. The unit could also be fabricated with a modified accumulation chamber having only one leg or without an accumulation chamber altogether. Another alternative arrangement would be to have the baffles joined to the humidifier top.

An advantage of the present invention over the prior art is that the latter provide only laminar air flow and thus, do not create sufficient turbulence to maximize humidification efficiency. The combination of channels and baffles creates increased turbulence. The total surface area of water is significantly greater than the prior art devices, further enhancing the rate of mass transfer.

Although the invention has been described in detail for the purpose of illustration, it is to be understood that such detail is solely for that purpose and that variations can be made therein by those skilled in the art without departing from the spirit and scope of the invention except as it may be limited to the claims.

What is claimed is:

1. A humidifier for adding moisture to an air flow comprising:

a body formed from a top wall, a substantially upright sidewall and a bottom wall for holding a supply of water having a free water surface;

an air inlet for supplying an air flow to the body;

an air outlet through which moisturized air is discharged from said body;

a plurality of parallel channel members extending from said top wall for forming a plurality of parallel longitudinal channels, at least one row of spaced apart baffles extending from said bottom wall towards said top wall, said at least one row of spaced apart baffles extending in a direction substantially transverse to said plurality of channel members, wherein the air flow passes through the plurality of channels over the baffles to create localized turbulence at the free water surface so as to promote moisturization of air flow; and an outlet chamber formed from a raised portion of said top wall, said chamber extending transversely to said plurality of channels and having a first portion open to at least two of said longitudinal channels and a second portion in communication with said outlet.

2. The humidifier of claim 1 wherein the outlet chamber is substantially U-shaped.

3. The humidifier of claim 1, wherein the outlet chamber is acoustically tuned to resonate in the frequency range which is known to be associated with upper airway obstructions.

\* \* \* \* \*